United States Patent [19]

Vályi et al.

[11] Patent Number: 4,614,652

[45] Date of Patent: Sep. 30, 1986

[54] COMPOSITIONS FOR THE POST-TREATMENT OF SEBORRHEAL, ACNEIFORM PROCESSES AND A PROCESS FOR THE PREPARATION THEREOF

[75] Inventors: Gabriella Vályi; Éva Kutassy, both of Debrecen, Hungary

[73] Assignee: Delta Vas-, Muanyag- ES Szolgaltato Ipari Szovetkezet, Tatabanya, Hungary

[21] Appl. No.: 651,608

[22] Filed: Sep. 17, 1984

[51] Int. Cl.[4] ............................................ A61K 35/78
[52] U.S. Cl. ................................ 424/195.1; 514/859; 514/864
[58] Field of Search ...................................... 424/195.1

[56] References Cited

FOREIGN PATENT DOCUMENTS 0061508 3/1981 European Pat. Off. .
1617532 4/1971 Fed. Rep. of Germany .
30811 12/1965 German Democratic Rep. .

OTHER PUBLICATIONS

Chemical Abstracts 50, 1991e (Pharm. Weekblad 90, 777–782, 1955).
Chemical Abstracts 69, 30067u (Rom. Pat. No. 48.101, 1967).
Chemical Abstracts, 78, 115107t (Riv. Ital. Essenze, Profumi, Piante Off., Aromi, Saponi, Cosmet., Aerosol 1972, 54, 740–743.
Chemical Abstracts 95, 68027f (Czech Pat. No. 185.262, 1980).
Chemical Abstracts 96, 205215c (Fr. Demande FR2, 488.132, 1982).
Die Pharmazie, 1979, Paintz et al., Zur lokalanaesthetischen Workung von Propolis und einigen Inhaltsstoffen, pp. 839–841.
Die Pharmazie, 1975, vol. 30, p. 803.
Hagers Handbuch der Pharmazeutischen Praxis, p. 505, 1971.
Handbuch der Kosmetika und Riechstoffe, vol. 3, Janistyn, pp. 631, 633, 640, 660, 661.
Austria–Codex 1983/1984, pp. 233, 489, 533 and 896–897.

Primary Examiner—Donald B. Moyer
Assistant Examiner—John W. Rollins, Jr.
Attorney, Agent, or Firm—Karl F. Ross; Herbert Dubno

[57] ABSTRACT

The invention relates to a cosmetic composition for the post-treatment of seborrheal, acneiform processes, characterized by containing (i) an extract of dried chamomile (*Matricaria chamomilla*) and dried St. John's wort (*Hypericum perforatum*) in apple brandy and/or gooseberry brandy,
(ii) an extract of propolis in apple brandy and/or gooseberry brandy, and
(iii) a known ceratoplastic agent.

11 Claims, No Drawings

COMPOSITIONS FOR THE POST-TREATMENT OF SEBORRHEAL, ACNEIFORM PROCESSES AND A PROCESS FOR THE PREPARATION THEREOF

The invention relates to cosmetic compositions for the post-treatment of seborrheal, acneiform processes and a process for the preparation thereof.

Seborrhea is a harmful process based on the excessive function of the sebaceous glands of the skin. The inflammation arising around the obstructed, untreated mass of sebum, followed by suppuration of the surrounding follicles and tissues is called acne (comedo). If not properly treated, long-lasting inflammation occurs which may result in scar formation. For stopping or mitigating these changes of the skin, cosmetic, or sometimes medical treatments are also needed.

For the treatment of seborrheic, acneiform skin surfaces generally shaking-mixtures or pastes are used which contain antiseptic, skin-sedative or desquamative agents. The post-treatment of the inflamed surfaces following such treatments and the removal of the traces of comedones cause, however, serious further problems. There is a need for cosmetic preparations which do not only eliminate the inflammation and suppurations, but which also rapidly heal the inflamed surfaces, without leaving beind traces.

It has been recognised that the above-mentioned need can be met by a cosmetic compositon containing
(i) an extract of dried chamomile (*Matricaria chamomilla*) and dried St. John's wort (*Hypericum perforatum*) in apple brandy and/or gooseberry brandy,
(ii) an extract of propolis in apple brandy and/or gooseberry brandy, and
(iii) a known ceratoplastic agent.

Accordingly, the subject of the present invention is a cosmetic composition. This composition is characterized by containing
(i) an extract of dried chamomile (*Matricaria chamomilla*) and dried St. John's wort (*Hypericum perforatum*) in apple brandy and/or gooseberry brandy,
(ii) an extract of propolis in apple brandy and/or gooseberry brandy, and
(iii) a known ceratoplastic agent.

Component (i) of the composition of the invention may contain an extract of at least one of dried peppermint (*Mentha piperita*), dried marigold (*Calendula officinalis*) and dried thyme (*Thymi vulgaris*) in apple brandy and/or gooseberry brandy.

One of the preferred forms of the cosmetic compositions of the present invention is a paint which is characterized by containing as component (i) an extract of 10 to 40 parts by weight of dried chamomile and 10 to 40 parts by weight of dried St. John's wort in 1000 parts by weight of apple brandy and/or gooseberry brandy of 40 to 50% alcohol content, as component (ii) an extract of 100 to 500 parts by weight of propolis in 1000 parts by weight of apple brandy and/or gooseberry brandy of 40 to 50% alcohol content and of a pH of about 7, and as component (iii) a ceratoplastic agent, preferably sulphur or a sulphur derivative.

This paint may contain in component (i) an extract of at least one of 10 to 40 parts by weight of dried peppermint, 10 to 40 parts by weight of dried marigold and 10 to 40 parts by weight of dried thyme.

Another preferred form of the cosmetic compositions of the present invention is a shaking mixture which is characterized by containing the above painter together with 10 to 80% by weight, based on the amount of said paint, of a known shaking mixture additive of a drying and skin-relaxing effect, preferably zinc oxide or talcum, and optionally 1 to 3% by weight of a disperging agent, preferably colloidal silicic acid, and 5 to 10% by weight of glycerol.

Another one of the preferred forms of the cosmetic compositions of the present invention is a paste which is characterized by containing the above shaking mixture together with 10 to 30% by weight, based on the amount of said shaking mixture, of a known hydrophilic anionic lanolin-lackng paste base material and 10 to 20% by weight of powder.

The above-described paint is prepared according to the invention as follows:
(a) To 1000 parts by weight of apple brandy or gooseberry-brandy of 40-50% alcohol content or to a mixture of any ratio of these brandies
10 to 40 parts by weight of dried chamomile flower,
10 to 40 parts by weight of dried St. John's wort,
and optionally at least one of
10 to 40 parts by weight of dried peppermint,
10 to 40 parts by weight of marigold and
10 to 40 parts by weight of dried thyme
are added, then this mixture is allowed to stand preferably at room temperature for 7 to 14 days and finally it is filtered.

(b) To 1000 parts by weight of apple brandy or gooseberry brandy of 40-50% alcohol content, adjusted preferably to pH 7, or to a mixture of any ratio of these brandies 100 to 500 parts by weight of propolis is added, then this mixture is allowed to stand preferably at room temperature over 7 to 14 days and finally it is filtered.

(c) The drug extract obtained in step (a) and the propolis extract obtained in step (b) are mixed together at a ratio of 60:40-80:20, and then 1-5% of a known ceratoplastic additive with possible antiseptic effect, preferably sulphur or a sulphur derivative such as bitumen-sulphonic acid ammonium salt, is added as the third component.

The shaking mixture is prepared according to the invention by adding to the paint prepared as described just above a known shaking mixture additive of drying and skin-relaxing effect, preferably zinc oxide or talcum, in an amount of 10 to 30% as related to the weight of the paint, furthermore 1 to 3% by weight of a disperging agent, preferably colloidal silicic acid, and 5 to 10% by weight of glycerol are also added, if needed.

The past is prepared according to the invention by adding to the shaking mixture prepared as described just above a known hydrophilic anionic lanolin-lacking paste base material in an amount of 10 to 80% as related to the weight of the shaking mixture, and 10-20% by weight of powder.

The paint, shaking mixture and paste prepared as described above stimulate and complement the effects of each other, giving a good chance for the post-treatment of the earlier mentioned skin diseases, following the treatment of the physician or cosmetician. This post-treatment can also be carried out by the patient themselves, at home. The compositions of the invention rapidly eliminate the inflammation, prevent the suppuration, dry the erosed epithel, accelerate its desquamation and promote the formation of the new epidermis. On the skin surfaces treated with such compositions there remain no, or substantially less scars, since the compositions initiate the regeneration of the skin and the tissues. The time needed for healing in case of post-treatment with the compositions of the invention is, in general, between 48 and 72 hours.

For preparing the propolis extract, apple brandy or gooseberry brandy is used the pH of which is adjusted preferably to 7.0. The use of these brandies as extracting agent is highly advantageous since they provide better extraction of the flavonoids, which play an important role in curing the acneiform skin-sites, and in stopping the inflammation.

As propolis a propolis collected, preferably in Central Europe, by the method described in the book "Honey propolis" issued by the editory "Apimondia", Bucharest, Roumania, in 1982 is used.

Among the active agents of the preparations, the antiseptic, antiinflammatory and epithel-formation promoting effects of the medicinal herbs are significantly increased by using said apple brandy or gooseberry brandy for the extraction. Experiments have also been carried out whereby the apple brandy or the gooseberry brandy was replaced by 50% alcohol for preparing the drug and propolis extracts. It was found that though the inflammation had stopped, the formation of epithel did not proceed to such extent as in the case of the compositions of the invention prepared with the aid of said brandies.

The invention is illustrated by the aid of the following non-limiting examples:

EXAMPLE 1

Preparation of basic solutions (a) To 1000 g. of gooseberry brandy of 50% alcohol content 20 g. of each of the following dried drugs are added: chamomile flower, peppermint, marigold, thyme and St. John's wort. The mixture is allowed to stand at room temperature for 10 days and then filtered.

(b) To 1000 g. of gooseberry brandy of 50% alcohol content, adjusted to pH 7.0 by triethanol amine, 500 g. of propolis are added. The mixture is allowed to stand for 10 days at room temperature and then filtered.

In this example, apple brandy may also be used instead of gooseberry brandy.

EXAMPLE 2

Preparation of a paint

To 78 g. of the drug extract prepared as in part (a) of Example 1 20 g. of the propolis extract prepared as in part (b) of Example 1 and 2 g. of a 50% aqueous solution of bituminous sulphonic acid ammonium salt (Ichtyol) are added.

A seborreic, acneiform skin surface to be treated is painted expediently twice a day with the painter prepared as above.

EXAMPLE 3

Preparation of a shaking mixture

To 75 g. of the painter prepared as in Example 2 5 g. of glycerol, 10 g. of zinc oxide, 10 g. of talcum and 2 g. of collodial silicic acid (Aerosil) are added and thoroughly mixed.

The shaking mixture prepared as above is a well-adhering suspension which complements well the effect of the paint in more severe cases. It is applied onto the inflamed skin surface after drying of the paint.

EXAMPLE 4

Preparation of a paste 50 g. of the shaking mixture prepared as in Example 3 is thoroughly mixed with 35 g. of hydrophilic, anionic paste base material (Unguentum hydrophilicum anionicum, Formulae Normales, Edition V, p. 451, 1967) and 15 g. of a dark-colored powder (a product of the Hungarian cosmetical firm CAOLA, containing among other components talcum, MgO and ZnO).

The paste prepared as above is suitable for the daytime treatment of seborrheic, acneiform skin surfaces. In addition to the above effect, it also improves the psychic state of the patient because its color is similar to that of the skin, so that the affected skin surface is cosmetically covered.

What is claimed is:

1. A process for the preparation of a paint suitable for the post-treatment of seborrheal, acneiform processes, which comprises the steps of:
   (a) adding to 1000 parts by weight of apple brandy or gooseberry brandy of 40–50% alcohol content
      10 to 40 parts by weight of dried chamomile,
      10 to 40 parts by weight of dried St. John's wort, then
      allowing the mixture to stand for 7–14 days and filtering,
   (b) adding to 1000 parts by weight of apple brandy or gooseberry brandy of 40–50% alcohol content or to a mixture of any ratio of these brandies 100 to 500 parts by weight of propolis, then allowing the mixture to stand for 7 to 14 days and filtering, and
   (c) mixing the drug extract according to (a) and the propolis extract according to (b) together in a volume ratio of 60:40 to 80:20 and adding to the thus-obtained mixture 1 to 5% of a ceratoplastic additive.

2. A process for the preparation of a shaking mixture suitable for the post-treatment of seborrheal, acneiform processes, which comprises adding to the paint prepared as claimed in claim 1, based on its weight, 10–30% by weight of a shaking mixture additive with drying and skin-relaxing effect.

3. A process for the preparation of a paste suitable for the post-treatment of seborreal, acneiform processes, which further comprises adding to the shaking mixture prepared as claimed in claim 2, based on its weight, 10–80% by weight of a hydrophilic anionic lanolin-lacking paste base material and 10–20% by weight of a pharmaceutically acceptable inert powder.

4. A cosmetic composition in the form of a paint for the post-treatment of seborrheal, acneiform processes, which comprises:
   (a) an extract of 10 to 40 parts by weight of dried chamomile and 10 to 40 parts by weight of dried St. John's wort in 1000 parts by weight of apple brandy or gooseberry brandy of 40 to 50% alcohol content as component (a);
   (b) an extract of 100 parts to 500 parts by weight of propolis in 1000 parts by weight apple brandy or gooseberry brandy of 40 to 50% alcohol content at a pH of about 7 as component (b); and
   (c) a ceratoplastic agent as component (c); wherein component (a) and component (b) are present in a weight ratio of 60:40 to 80:20, and wherein the ceratoplastic agent constitutes 1 to 5% by weight of the composition.

5. The cosmetic composition defined in claim 4 wherein component (a) further comprises at least one of the following: 10 to 40 parts by weight of dried peppermint; 10 to 40 parts by weight of marigold; and 10 to 40 parts by weight of dried thyme.

6. The composition defined in claim 4 wherein the ceratoplastic agent is sulfur or bitumen-sulphonic acid ammonium salt.

7. A cosmetic composition in the form of a shaking mixture which comprises the cosmetic composition in the form of a paint as defined in claim 4 in combination with 10 to 30% by weight, based on the amount of the paint composition of a shaking mixture additive of a drying or a skin-relaxing effect.

8. The cosmetic composition in the form of a shaking mixture defined in claim 7 which comprises zinc oxide or talc as the shaking mixture additive.

9. The cosmetic composition in the form of a shaking mixture defined in claim 7 further comprising 1 to 3% by weight of a disperging agent and 5 to 10% by weight glycerol.

10. A cosmetic composition in the form of a paste which comprises the cosmetic composition in the form of a shaking mixture defined in claim 7 together with 10 to 50% by weight, based on the amount of the shaking mixture, of a hydrophilic, anionic, lanolin-lacking paste base material and 10 to 20% by weight of a pharmaceutically acceptable inert powder.

11. The cosmetic composition defined in claim 10 which comprises as a pharmaceutically acceptable inert powder a powder containing talc, magnesium oxide or zinc oxide.

* * * * *